(12) United States Patent
LaNeve et al.

(10) Patent No.: US 11,931,053 B2
(45) Date of Patent: Mar. 19, 2024

(54) SINGLE-USE JOINT DECORTICATOR APPARATUS

(71) Applicant: PTL Opco, LLC, Tampa, FL (US)

(72) Inventors: Sean LaNeve, Tampa, FL (US);
Dwayne Polzer, Lutz, FL (US);
Christopher Lee, Tampa, FL (US)

(73) Assignee: PTL Opco, LLC, Tampa, FL (US)

( * ) Notice: Subject to any disclaimer, the term of this patent is extended or adjusted under 35 U.S.C. 154(b) by 0 days.

(21) Appl. No.: 18/221,347

(22) Filed: Jul. 12, 2023

(65) Prior Publication Data
US 2024/0041476 A1 Feb. 8, 2024

Related U.S. Application Data

(60) Provisional application No. 63/395,270, filed on Aug. 4, 2022.

(51) Int. Cl.
*A61B 17/16* (2006.01)
*A61F 2/46* (2006.01)
(Continued)

(52) U.S. Cl.
CPC ........ *A61B 17/1659* (2013.01); *A61F 2/4603* (2013.01); *A61B 2017/0023* (2013.01);
(Continued)

(58) Field of Classification Search
CPC ........................... A61F 17/1671; A61F 2/4603
See application file for complete search history.

(56) References Cited

U.S. PATENT DOCUMENTS

| 4,569,338 A | 2/1986 | Edwards |
| 5,334,205 A | 8/1994 | Cain |

(Continued)

FOREIGN PATENT DOCUMENTS

| AU | 726979 | 10/1998 |
| AU | 756550 | 5/2002 |

(Continued)

OTHER PUBLICATIONS

Steven P. Cohen, MD, Sacroiliac Joint Pain: A Comprehensive Review of anatomy, Diagnosis, and Treatment, Review Article, Apr. 27, 2005, 1440-1453, vol. 101, International Anesthesia Research Society, United States.

(Continued)

*Primary Examiner* — Andrew Yang
(74) *Attorney, Agent, or Firm* — Stephen E. Kelly; Andriy Lytvyn; Hill Ward Henderson, P.A.

(57) ABSTRACT

A joint decorticator instrument configured for single use. The joint decorticator has a metal rod affixed within a polymer sheath. The polymer sheath has a longitudinal channel configured to receive an alignment protrusion with a working channel for maintaining the joint decorticator in a proper alignment relative to the working channel. The joint decorticator may include an integrated extraction mechanism involves an extraction lever pivotally connected to the handle portion of the polymer sheath. The extraction lever has an eccentric cam mechanism. When the extraction lever is pivoted toward an open position, the cam exerts a force onto a collar of the working channel and an opposite force on the connector pin that pivotally connects the extraction lever to the polymer sheath, thereby dislodging the abrading head of the joint decorticator from the joint.

22 Claims, 12 Drawing Sheets

(51) Int. Cl.
    *A61B 17/00*           (2006.01)
    *A61B 17/56*           (2006.01)
    *A61F 2/30*            (2006.01)

(52) U.S. Cl.
    CPC .............. *A61B 2017/00367* (2013.01); *A61B 2017/0042* (2013.01); *A61B 2017/564* (2013.01); *A61F 2002/30622* (2013.01)

(56) References Cited

U.S. PATENT DOCUMENTS

| | | |
|---|---|---|
| 5,722,978 A | 3/1998 | Jenkins, Jr. |
| 6,080,155 A | 6/2000 | Michelson |
| 6,371,988 B1 | 4/2002 | Pafford et al. |
| 6,436,098 B1 | 8/2002 | Michelson |
| 6,648,917 B2 | 11/2003 | Gerbec et al. |
| 6,652,533 B2 | 11/2003 | O'Neil |
| 6,770,074 B2 | 8/2004 | Michelson |
| 6,846,327 B2 | 1/2005 | Khandkar et al. |
| 7,018,416 B2 | 3/2006 | Hanson et al. |
| 7,125,425 B2 | 10/2006 | Foley et al. |
| 7,390,327 B2 | 6/2008 | Collazo et al. |
| 7,648,509 B2 | 1/2010 | Stark |
| 8,016,829 B2 | 9/2011 | Mahoney et al. |
| 8,021,392 B2 | 9/2011 | Petersen |
| 8,025,684 B2 | 9/2011 | Garcia-Bengochea et al. |
| 8,128,700 B2 | 3/2012 | Delurio et al. |
| 8,157,865 B2 | 4/2012 | Hochschuler et al. |
| 8,162,981 B2 | 4/2012 | Vestgaarden |
| 8,197,513 B2 | 6/2012 | Fisher et al. |
| 8,221,503 B2 | 7/2012 | Garcia et al. |
| 8,348,950 B2 | 1/2013 | Assell et al. |
| 8,403,991 B2 | 3/2013 | Ullrich, Jr. et al. |
| 8,551,171 B2 | 10/2013 | Johnson et al. |
| 8,556,900 B2 | 10/2013 | Yoko et al. |
| 8,579,912 B2 | 11/2013 | Isaza et al. |
| 8,623,053 B2 | 1/2014 | Vestgaarden |
| 8,623,054 B2 | 1/2014 | McCormack et al. |
| 8,740,912 B2 | 6/2014 | Stark |
| 8,753,345 B2 | 6/2014 | McCormack et al. |
| 8,753,347 B2 | 6/2014 | McCormack et al. |
| 8,828,062 B2 | 9/2014 | McCormack et al. |
| 8,834,472 B2 | 9/2014 | McCormack et al. |
| 8,882,818 B1 | 11/2014 | Vestgaarden |
| 8,906,025 B2 | 12/2014 | Yoko et al. |
| 8,906,028 B2 | 12/2014 | Kleiner et al. |
| 8,945,224 B2 | 2/2015 | Trieu |
| 8,961,571 B2 | 2/2015 | Lee et al. |
| 8,979,928 B2 | 2/2015 | Donner |
| 9,005,288 B2 | 4/2015 | McCormack et al. |
| 9,011,492 B2 | 4/2015 | McCormack et al. |
| 9,017,407 B2 | 4/2015 | Donner |
| 9,101,371 B2 | 8/2015 | Assell et al. |
| 9,119,732 B2 | 9/2015 | Schifano et al. |
| 9,186,155 B2 | 11/2015 | Katzman et al. |
| 9,241,798 B2 | 1/2016 | Petersen |
| 9,247,943 B1 | 2/2016 | Kleiner |
| 9,320,529 B2 | 4/2016 | Yoko et al. |
| 9,345,525 B2 | 5/2016 | Yoko et al. |
| 9,375,243 B1 | 6/2016 | Vestgaarden |
| 9,421,109 B2 | 8/2016 | Donner |
| 9,451,986 B2 | 9/2016 | Stoffman |
| 9,492,284 B2 | 11/2016 | Ginn et al. |
| 9,622,791 B2 | 4/2017 | McCormack et al. |
| 9,629,665 B2 | 4/2017 | McCormack et al. |
| 9,662,128 B2 | 5/2017 | Reiley |
| 9,668,781 B2 | 6/2017 | Stark |
| 9,675,363 B2 | 6/2017 | Abbasi |
| 9,700,356 B2 | 7/2017 | Donner et al. |
| 9,757,154 B2 | 9/2017 | Donner et al. |
| 9,795,396 B2 | 10/2017 | Donner et al. |
| 9,801,732 B2 | 10/2017 | Chin et al. |
| 9,808,346 B2 | 11/2017 | Stark |
| 9,833,321 B2 | 12/2017 | Rindal |
| 9,883,874 B1 | 2/2018 | Vestgaarden |
| 9,895,176 B2 | 2/2018 | Vestgaarden |
| 9,949,843 B2 | 4/2018 | Reiley et al. |
| 10,004,547 B2 | 6/2018 | Reiley |
| 10,070,970 B2 | 9/2018 | Lynn et al. |
| 10,123,849 B2 | 11/2018 | Greenhalgh et al. |
| 10,136,932 B2 | 11/2018 | Freese |
| 10,149,673 B2 | 12/2018 | McCormack et al. |
| 10,149,764 B2 | 12/2018 | Stark |
| 10,166,033 B2 | 1/2019 | Reiley et al. |
| 10,195,053 B2 | 2/2019 | Kleiner et al. |
| 10,201,427 B2 | 2/2019 | Mauldin |
| 10,206,739 B2 | 2/2019 | Godara et al. |
| 10,219,841 B1 | 3/2019 | Compton et al. |
| 10,219,912 B2 | 3/2019 | Suh et al. |
| 10,226,285 B2 | 3/2019 | McCormack et al. |
| 10,245,044 B2 | 4/2019 | Petersen |
| 10,265,176 B2 | 4/2019 | Donner et al. |
| 10,292,720 B2 | 5/2019 | Donner |
| 10,314,710 B2 | 6/2019 | Donner et al. |
| 10,321,945 B2 | 6/2019 | Schifano et al. |
| 10,357,368 B2 | 7/2019 | Aksu |
| 10,363,140 B2 | 7/2019 | Mauldin et al. |
| 10,398,425 B2 | 9/2019 | Mahoney et al. |
| 10,426,539 B2 | 10/2019 | Schifano et al. |
| 10,456,175 B2 | 10/2019 | McCormack et al. |
| 10,492,802 B2 | 12/2019 | Donner et al. |
| 10,543,105 B2 | 1/2020 | Greenhalgh et al. |
| 10,555,818 B2 | 2/2020 | McConnell et al. |
| 10,568,666 B2 | 2/2020 | McCormack et al. |
| 10,588,672 B2 | 3/2020 | McCormack et al. |
| 10,646,258 B2 | 5/2020 | Donner et al. |
| 10,653,535 B2 | 5/2020 | McCormack et al. |
| 10,682,150 B2 | 6/2020 | Stark |
| 10,736,752 B1 | 8/2020 | Schifano et al. |
| 10,751,196 B1 | 8/2020 | Schifano et al. |
| 10,765,532 B2 | 9/2020 | Ashleigh et al. |
| 10,779,958 B2 | 9/2020 | Lines |
| 10,820,917 B2 | 11/2020 | Sharifi-Mehr et al. |
| D905,232 S | 12/2020 | Schifano et al. |
| 10,864,021 B2 | 12/2020 | Marik et al. |
| 10,952,749 B2 | 3/2021 | Abbasi |
| 10,993,757 B2 | 5/2021 | Schifano et al. |
| D922,568 S | 6/2021 | Schifano et al. |
| 11,058,556 B2 | 7/2021 | LaNeve et al. |
| 11,083,511 B2 | 8/2021 | Schifano et al. |
| 11,141,144 B2 | 10/2021 | McCormack et al. |
| 11,272,964 B2 | 3/2022 | McCormack et al. |
| 11,344,339 B2 | 5/2022 | McCormack et al. |
| 11,376,026 B2 | 7/2022 | Donner et al. |
| D972,137 S | 12/2022 | Schifano et al. |
| 11,547,424 B2 | 1/2023 | Ries |
| 11,559,408 B2 | 1/2023 | McCormack et al. |
| 11,583,416 B2 | 2/2023 | Greenhalgh et al. |
| 11,666,362 B2 | 6/2023 | Compton et al. |
| 2001/0000532 A1 | 4/2001 | Michelson |
| 2001/0031967 A1 | 10/2001 | Nicholson et al. |
| 2005/0075640 A1 | 4/2005 | Collazo et al. |
| 2005/0080422 A1 | 4/2005 | Otte et al. |
| 2005/0165420 A1 | 7/2005 | Cha |
| 2005/0240195 A1 | 10/2005 | Axelson, Jr. et al. |
| 2005/0251146 A1 | 11/2005 | Martz et al. |
| 2006/0054171 A1 | 3/2006 | Dall |
| 2006/0089633 A1 | 4/2006 | Bleich et al. |
| 2006/0178673 A1 | 8/2006 | Curran et al. |
| 2007/0156241 A1 | 7/2007 | Reiley et al. |
| 2007/0233131 A1 | 10/2007 | Song et al. |
| 2008/0009861 A1 | 1/2008 | Stark |
| 2008/0154374 A1 | 6/2008 | Labrom |
| 2008/0249569 A1 | 10/2008 | Waugh et al. |
| 2009/0024174 A1 | 1/2009 | Stark |
| 2009/0076551 A1 | 3/2009 | Petersen |
| 2009/0099610 A1 | 4/2009 | Johnson et al. |
| 2009/0216238 A1 | 8/2009 | Stark |
| 2009/0259261 A1 | 10/2009 | Reiley |
| 2009/0312763 A1 | 12/2009 | McCormack et al. |
| 2011/0098817 A1 | 4/2011 | Eckhardt |
| 2011/0106261 A1 | 5/2011 | Kingsley et al. |
| 2011/0238181 A1 | 9/2011 | Trieu |
| 2011/0264229 A1 | 10/2011 | Donner |

(56) References Cited

U.S. PATENT DOCUMENTS

| | | |
|---|---|---|
| 2012/0083883 A1 | 4/2012 | Ginn |
| 2012/0259365 A1 | 10/2012 | Richelsoph |
| 2012/0277801 A1 | 11/2012 | Marik |
| 2013/0006368 A1 | 1/2013 | Walsh et al. |
| 2013/0144296 A1 | 6/2013 | Yoko et al. |
| 2013/0144350 A1 | 6/2013 | Yoko et al. |
| 2013/0173004 A1 | 7/2013 | Greenhalgh et al. |
| 2013/0218215 A1 | 8/2013 | Ginn et al. |
| 2013/0325020 A1 | 12/2013 | Yoko et al. |
| 2014/0031935 A1 | 1/2014 | Donner et al. |
| 2014/0081279 A1 | 3/2014 | Kleiner et al. |
| 2014/0088711 A1 | 3/2014 | Kingsley et al. |
| 2014/0207191 A1 | 7/2014 | Kornel |
| 2014/0277204 A1 | 9/2014 | Sandu |
| 2015/0012097 A1 | 1/2015 | Ibarra et al. |
| 2015/0025534 A1 | 1/2015 | Gordan et al. |
| 2015/0073552 A1 | 3/2015 | To et al. |
| 2015/0080976 A1 | 3/2015 | Yoko et al. |
| 2015/0112444 A1 | 4/2015 | Aksu |
| 2015/0230937 A1 | 8/2015 | Voellmicke |
| 2015/0328012 A1 | 11/2015 | Hansell et al. |
| 2016/0030191 A1 | 2/2016 | McLuen et al. |
| 2016/0175113 A1 | 6/2016 | Lins |
| 2016/0310197 A1 | 10/2016 | Black et al. |
| 2017/0245999 A1 | 8/2017 | Ginn et al. |
| 2018/0036017 A1 | 2/2018 | Donner et al. |
| 2018/0092748 A1 | 4/2018 | Donner et al. |
| 2018/0161077 A1 | 6/2018 | McCormack et al. |
| 2018/0303624 A1 | 10/2018 | Shoshtaev |
| 2019/0021868 A1 | 1/2019 | Ludwig et al. |
| 2019/0083271 A1 | 3/2019 | Donner et al. |
| 2019/0090888 A1 | 3/2019 | Sand et al. |
| 2019/0133613 A1 | 5/2019 | Reiley et al. |
| 2019/0262010 A1 | 8/2019 | Cerundolo et al. |
| 2019/0336292 A1 | 11/2019 | Aksu |
| 2019/0343640 A1 | 11/2019 | Donner et al. |
| 2020/0029979 A1 | 1/2020 | Donner et al. |
| 2020/0085480 A1 | 3/2020 | Schifano et al. |
| 2020/0093612 A1 | 3/2020 | Blain et al. |
| 2020/0138589 A1 | 5/2020 | Abbasi |
| 2020/0179135 A1 | 6/2020 | Castro |
| 2020/0253619 A1 | 8/2020 | Gregory |
| 2020/0315811 A1 | 10/2020 | Cryder et al. |
| 2020/0390566 A1 | 12/2020 | Murray et al. |
| 2021/0015502 A1 | 1/2021 | Sharifi-Mehr et al. |
| 2021/0386434 A1 | 12/2021 | Tanaka et al. |
| 2022/0287742 A1 | 9/2022 | McCormack et al. |
| 2022/0313334 A1 | 10/2022 | Schifano et al. |
| 2023/0076180 A1 | 3/2023 | Schifano et al. |
| 2023/0157734 A1 | 5/2023 | McCormack et al. |

FOREIGN PATENT DOCUMENTS

| | | |
|---|---|---|
| CN | 110123436 | 8/2019 |
| EP | 1328216 A1 | 7/2003 |
| EP | 1290985 B1 | 4/2008 |
| EP | 1713408 B1 | 9/2010 |
| EP | 2328492 B1 | 3/2018 |
| EP | 2702952 B1 | 4/2018 |
| EP | 3326556 A1 | 5/2018 |
| EP | 2877128 B1 | 6/2018 |
| EP | 3641670 B1 | 4/2023 |
| FR | 2727004 | 5/1996 |
| WO | WO/2017066443 | 4/2017 |
| WO | WO/2018195406 | 10/2018 |
| WO | WO/2019137626 | 7/2019 |
| WO | WO/2021188823 A1 | 9/2021 |
| WO | WO/2022159837 | 7/2022 |

OTHER PUBLICATIONS

K. A. Giannikas, A. M. Khan, M.T. Karski, H. A. Maxwell, Sacroiliac joint fusion for chronic pain: a simple technique avoiding the use of metalwork, Journal, Nov. 28, 2003, 253-256, vol. 13, Springer-Verlag, Greece.

Captiva Spine, TransFasten Posterior Sacroiliac (SI) Joint Fusion System, available at, https://transfasten.captivaspine.com/si-joint-surgeon-providers/, last visited on Sep. 1, 2023.

International Search Report and Written Opinion for International Application No. PCT/US2023/029556, dated Nov. 17, 2023.

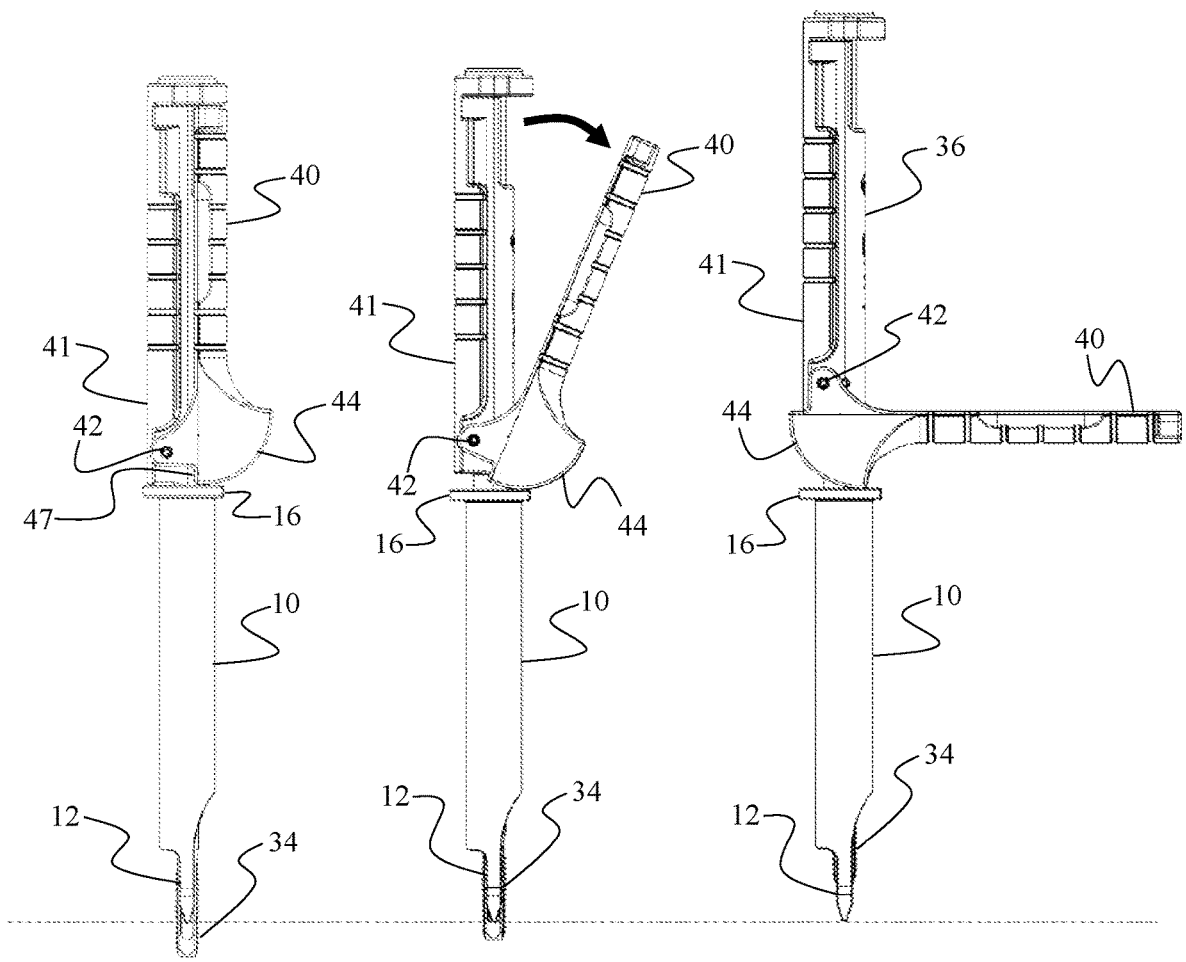
*FIG. 6A*  *FIG. 6B*  *FIG. 6C*

SINGLE-USE JOINT DECORTICATOR APPARATUS

CROSS-REFERENCE TO RELATED APPLICATION

This application is a non-provisional of and claims priority to the U.S. Provisional Application No. 63/395,270 filed on Aug. 4, 2022, the contents of which are incorporated herein by reference in their entireties.

BACKGROUND

(1) Field of Endeavor

The present invention relates generally to the field of medical devices, and more particularly, to a single-use joint decorticator apparatus and a method of use thereof.

(2) Description of Related Art

Minimally invasive posterior sacroiliac joint fusion procedures are effective at alleviating back pain. These procedures are performed using a set of surgical instruments that includes a working channel, a joint dilator, a joint decorticator, and an implant inserter. As the demand for the posterior sacroiliac joint fusion procedures grows, availability of surgery-ready instruments often becomes a limiting factor with respect to the frequency at which these procedures can be performed. After every procedure, the surgical instruments must undergo a sterilization process, which requires an autoclave and associated equipment. The autoclaving process is time consuming and expensive. Thus, there is an unresolved need for mass-produced, single-use surgical instruments that are surgery-ready on-demand.

Another unresolved need associated with sacroiliac joint fusion procedures pertains to extracting a joint decorticator from the joint. During a surgery, it is common for a joint decorticator to become lodged within a patient's joint. A common technique for extracting a lodged surgical instrument requires a surgeon to use a slide hammer connected to the proximal end of the surgical instrument. According to this technique, the surgeon grasps the hammer sleeve and repeatedly impacts the slide stop of the hammer by forcibly sliding the sleeve along the hammer shaft. However, the effectiveness of the slide hammer often depends on the slide having adequate mass to deliver the requisite impact force, and the heavy slide can cause the entire instrument to become unwieldy during use. Thus, the hammer shaft may exhibit wobbling behavior during the extraction procedure. Because the hammer shaft is connected to the surgical instrument, which is positioned within the working channel, the wobbling of the slide hammer may cause the surgical instrument, and even the working channel, to move erratically. Even a small degree of erratic movement may significantly decrease the amount of control the surgeon has over the surgical instrument, may cause an injury to the patient, and may displace the working channel.

Accordingly, what is needed is an improved, surgery-ready joint decorticator having an integrated extraction mechanism that facilitates safe and efficient extraction of the joint decorticator from a patient's joint and removal thereof via the working channel.

SUMMARY OF THE PREFERRED EMBODIMENTS

In the preferred embodiment, the system and instruments described herein comprises a working channel, a joint dilator, a joint decorticator, an extraction tool, and an implant inserter. The joint decorticator has a polymer sheath with a lumen. The polymer sheath has a distal end, a proximal end, and is configured to be inserted within the working channel to provide access to the joint. A metal rod with a first end and a second end is disposed within the lumen of the polymer sheath. An abrading head is disposed on the first end of the metal rod and extends beyond the distal end of the polymer sheath. The abrading head has abrading surfaces that are used to decorticate cortical bone tissue within the joint. The polymer sheath has a longitudinal channel for slidibly receiving an alignment protrusion of the working channel, when the decorticator apparatus is inserted therein. The longitudinal channel and the alignment protrusion work together to prevent rotation of the decorticator apparatus relative to the working channel and the joint.

The decorticator apparatus may include an extraction lever that is affixed to the polymer sheath. The extraction lever and the polymer sheath collectively define a handle of the joint decorticator. The extraction lever has a cam mechanism for retracting the decorticator apparatus from the working channel. When the extraction lever is transitioned from a closed position toward an open position, the cam mechanism of the extraction lever applies a retractive force onto the joint decorticator, thereby retracting the abrading head of the joint decorticator into the working channel and extracting the abrading head from the joint.

In an embodiment, an extraction tool is provided to facilitate extraction of the decorticator apparatus from the joint. The extraction tool can be used as a lever to simultaneously apply opposing forces to the decorticating apparatus and the working channel causing them to separate. In an embodiment, the extraction tool is configured to sequentially engage and apply a retractive force onto a first engagement surface of the decorticating apparatus, and then engage and apply a retractive force onto a second engagement surface of the decorticating apparatus, thereby incrementally extracting the decorticating apparatus from the working channel.

In an embodiment, the invention pertains to a method of preparing a joint for receiving a fusion implant. A working channel is positioned within the joint, providing a passage thereto. The abrading head of the decorticator apparatus is inserted into the working channel. The longitudinal channel with the polymer sheath receives an alignment protrusion of the working channel, thereby properly aligning the decorticator apparatus relative to the working channel. The decorticating apparatus is then advanced into the working channel. The abrading head of the decorticator apparatus is then driven into the joint thereby abrading cortical bone tissue within the joint. If necessary, an impact disk of the decorticator apparatus may be stricken with an impactor. The decorticator apparatus is then extracted using the extraction lever and cam mechanism. If necessary, the extraction tool is used to complete the extraction of the decorticator apparatus.

BRIEF DESCRIPTION OF THE DRAWINGS

FIG. 6A is the first figure in a sequence depicting a method of extracting the joint decorticator from the working channel using an extraction lever.

FIG. 6B is the second figure in the sequence depicting a method of extracting the joint decorticator from the working channel using the extraction lever.

FIG. 6C is the third figure in the sequence depicting a method of extracting the joint decorticator from the working channel using the extraction lever.

DESCRIPTION OF THE PREFERRED EMBODIMENT

With reference to the drawings, the novel and non-obvious surgical instrument having an integrated extraction mechanism will now be described with regard for the best mode and the preferred embodiment. The following discussion presents the surgical instrument in the context of the sacroiliac joint. However, the embodiments disclosed herein are meant for illustration and not limitation of the invention.

An ordinary practitioner will appreciate that it is possible to create many variations of the following embodiments without undue experimentation, and the instruments described herein can be used with surgical procedures at locations other than the sacroiliac joint.

Surgical Instrument Kit

Figure 1:
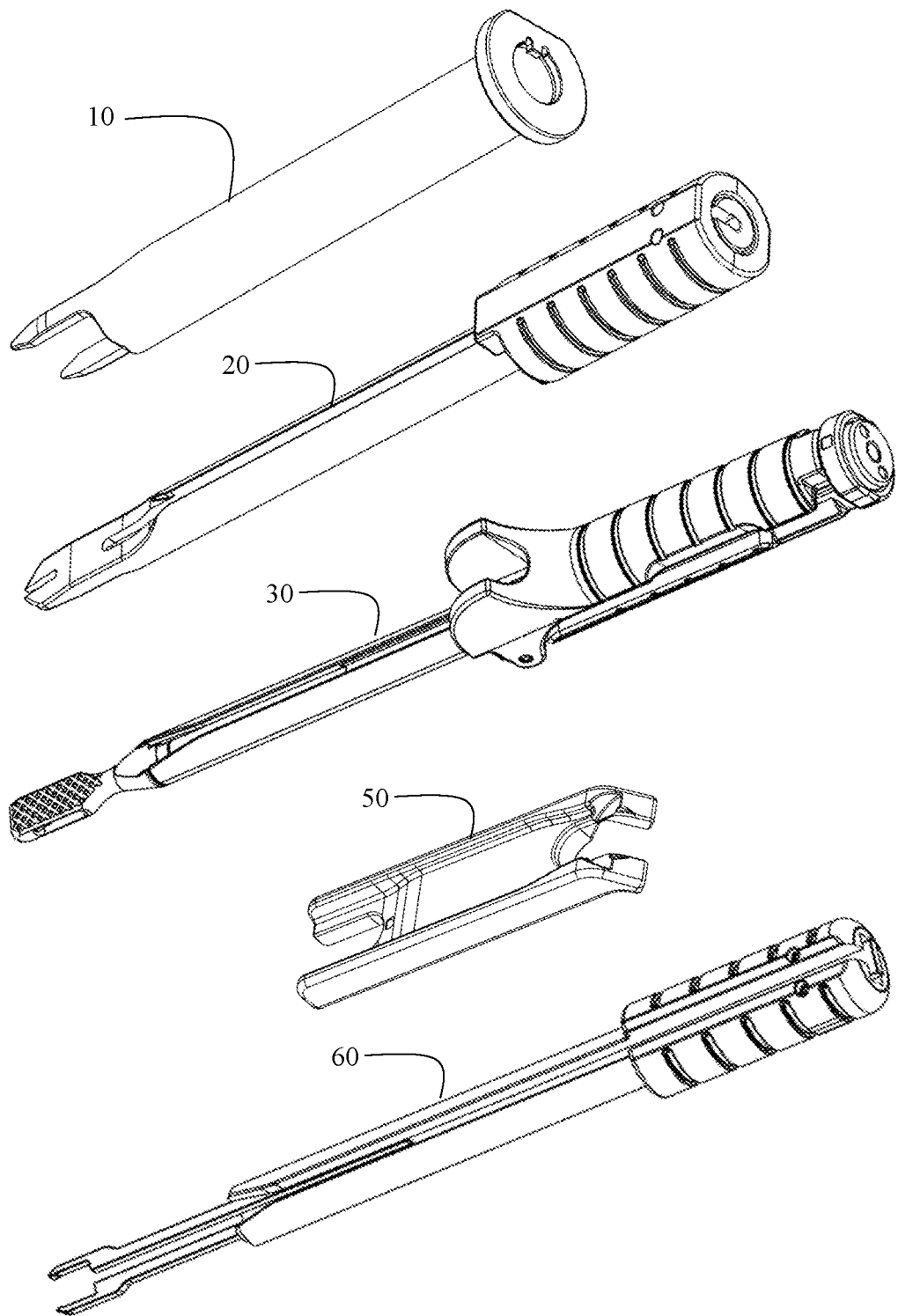
FIG. 1 depicts an embodiment of a surgical instrument set for performing a sacroiliac joint fusion procedure.

FIG. 1 depicts an embodiment of a surgical instrument kit for performing a minimally invasive, posterior sacroiliac joint fusion procedure. The kit includes a working channel 10, a joint dilator 20, a joint decorticator 30, an extraction tool 50, and an implant inserter 60. In some aspects these surgical tool are similar to the surgical tools disclosed in U.S. Pat. Nos. 11,020,129; 11,058,556; and 11,058,550, all of which are incorporated herein by reference, in their entireties.

Working Channel

Figure 2A:
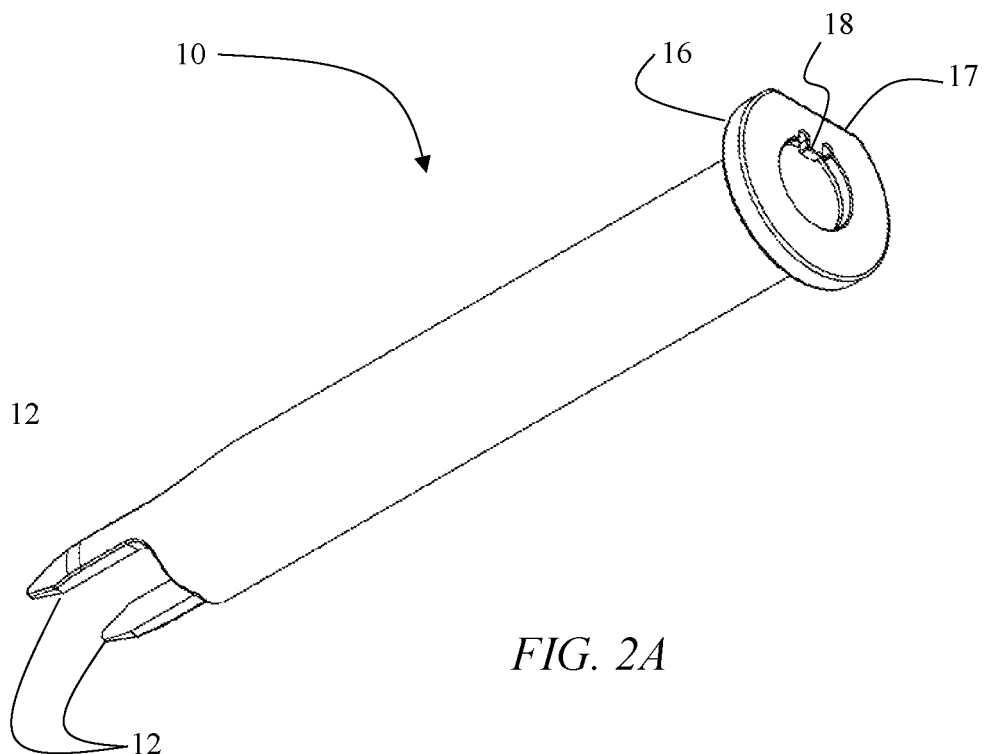
FIG. 2A is a perspective view of an embodiment of a working channel.
Figure 2B:
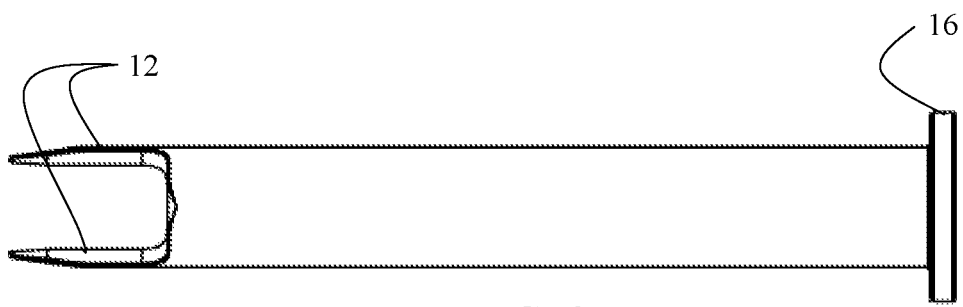
FIG. 2B is a top view of the embodiment of the working channel.
Figure 2C:
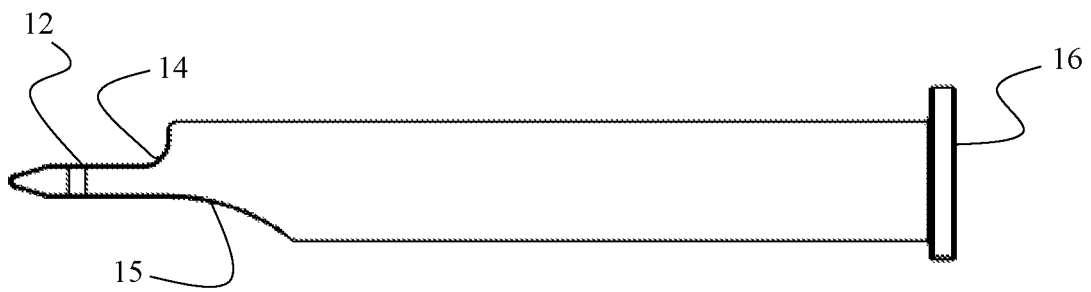
FIG. 2C is a side view of the embodiment of the working channel.

FIGS. 2A-2C depict a working channel 10 according to an embodiment of the invention. The working channel 10 has a pair of arms 12 configured for insertion between a patient's sacrum and ilium. The arms 12 interface with the working channel 10 in a manner that defines a sacral contour 14 and an iliac contour 15, which are configured for abutment against the sacrum and ilium, respectively. The working channel 10 has a collar 16. The collar 16 has a flat edge 17 aligned with the iliac contour 15, providing a visual and tactile reference indicating the radial orientation of the working channel 10. An alignment protrusion 18 is disposed within the collar 16 and serves as a keyway feature to maintain surgical instruments inserted into the working channel 10 in a predetermined radial orientation relative thereto.

Joint Dilator

Figure 3A:
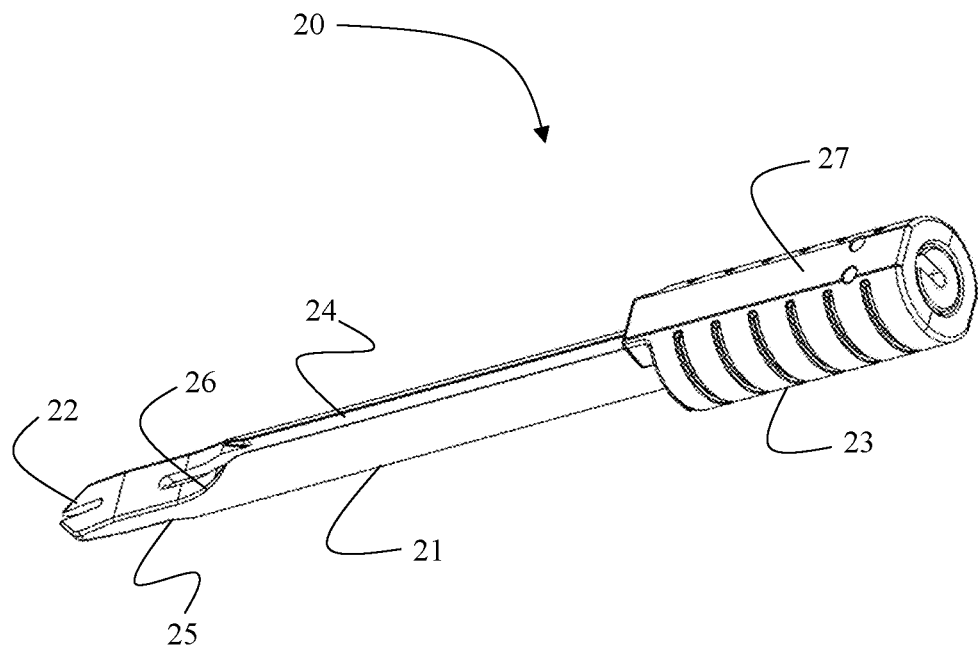
FIG. 3A is a perspective view of an embodiment of a joint dilator.
Figure 3B:
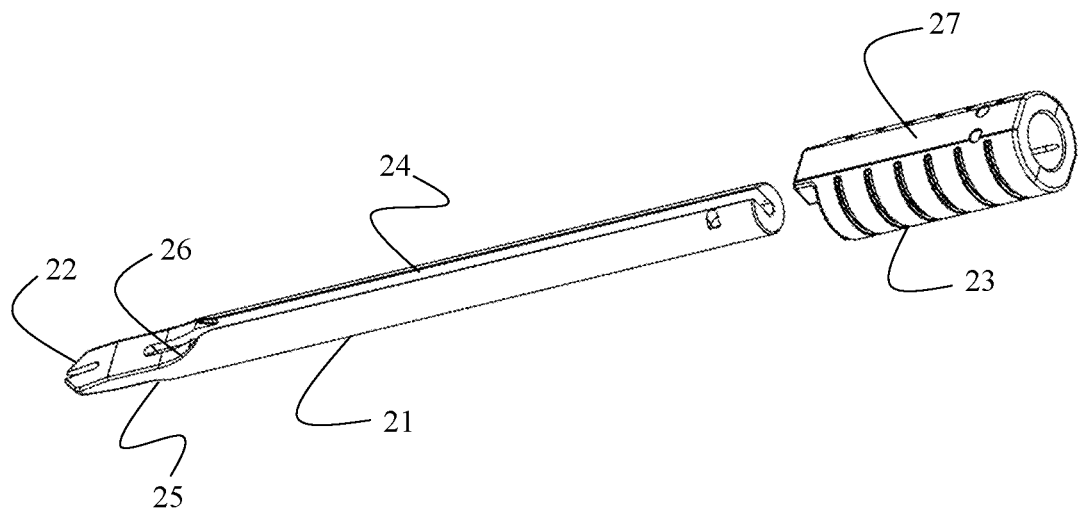
FIG. 3B is a perspective exploded view of the embodiment of the joint dilator.

FIGS. 3A-3B depict an embodiment of a joint dilator 20. The joint dilator has a generally cylindrical metal body 21. The metal body 21 has a beveled distal end 22 configured for spreading the soft tissue and sliding into a gap between the sacrum and ilium. The leading edge of the beveled distal end 22 is blunt to minimize the possibility of inadvertent penetration into bone tissue during insertion of the joint dilator 20 into the sacroiliac joint. A polymer handle 23 has an inner lumen for receiving the proximal end of the metal body 21 therein. The handle 23 may be affixed to the metal body 21 using fasteners, or any other affixing means known in the art. In an embodiment, the handle 23 has flat surfaces 27 that prevent the joint dilator 20 from rolling when placed on a surgical tray or another support surface. In addition, the flat surfaces 27 provide visual and tactile references with respect to the radial orientation of the joint dilator 20. Furthermore, the flat surfaces 27 enable the joint dilator 20 to be used as an impactor for driving the joint decorticator 30 into the joint, wherein the metal body 21 is functions as a handle, while handle 23 becomes the impactor head.

The metal body 21 has a channel 24 extending its full length or a portion thereof, especially the distal portion thereof. The channel 24 is configured to receive a K-wire therein for guiding the joint dilator 20 toward a predetermined location within the sacroiliac joint. At the distal end of the joint dilator 20, a section of the channel 24 may be fully enclosed to restrict non-axial movement of the K-wire within the channel 24. The remainder of the channel 24 is open to enable the soft tissue and bodily fluids displaced during the insertion of the joint dilator 20 to exit the channel 24.

Figure 4A:
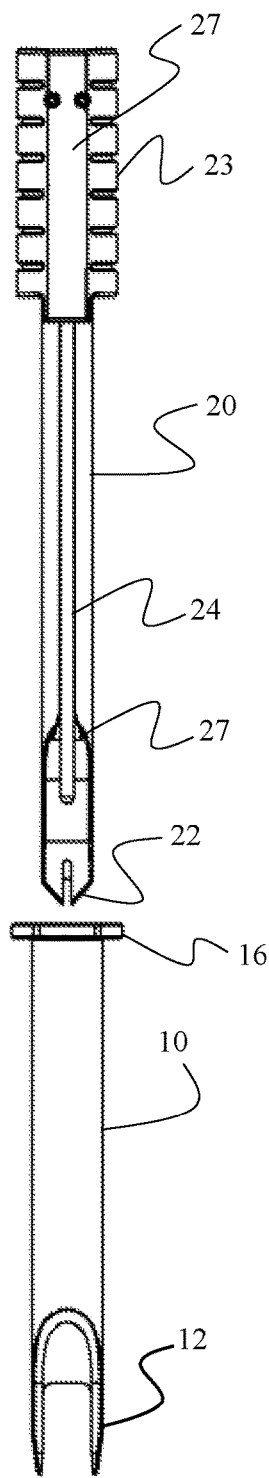
FIG. 4A is the first figure in a sequence depicting a method of inserting a joint dilator into a working channel.
Figure 4B:
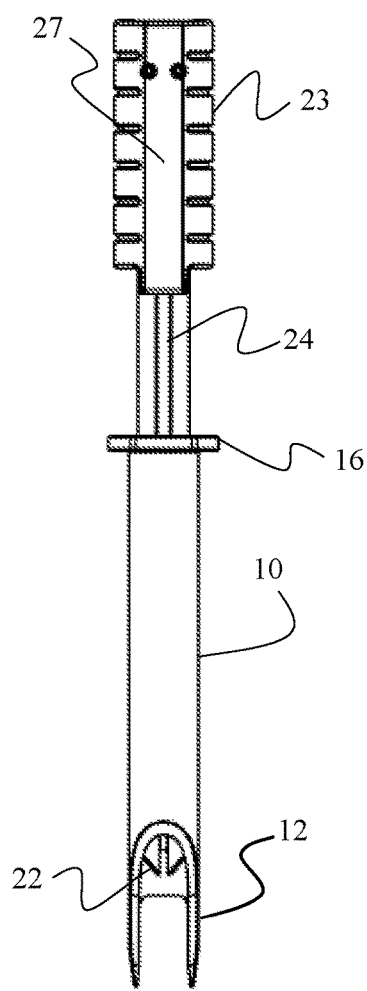
FIG. 4B is the second figure in the sequence depicting the method of inserting the joint dilator into the working channel.
Figure 4C:
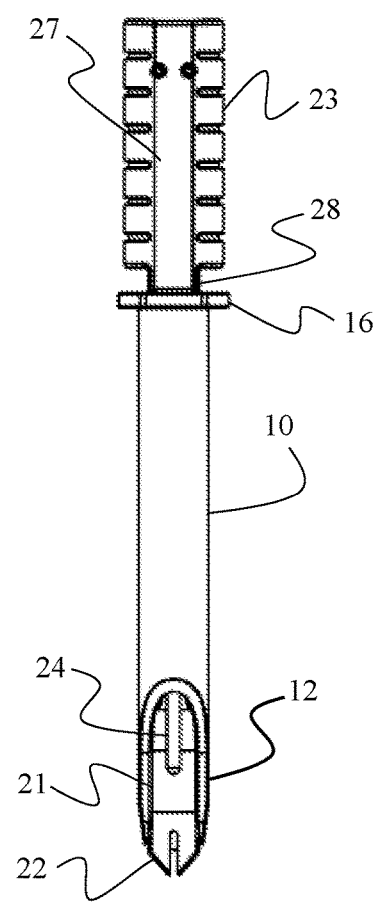
FIG. 4C is the third figure in a sequence depicting the method of inserting the joint dilator into the working channel.

FIGS. 4A-4C illustrate the steps of the joint dilator 20 being coupled with the working channel 10 to collectively form a joint dilator assembly. The channel 24 receives the alignment protrusion 18 of the working channel 10 thereby restraining the joint dilator 20 against relative rotation with respect to the working channel 10. The channel 24 may have a flared section 27—for example, delta-shaped—for helping guide the alignment protrusion 18 into the channel 24.

The distal end of the joint dilator 20 has sacral and iliac contours 25 and 26 that complement the sacral and iliac contours 12 and 14 of the working channel 10. FIG. 4C depicts that the clearances between the inner surfaces of arms 12 and the metal body 21 are minimal to prevent pinching of soft tissue therebetween. In an embodiment, the lateral walls of the distal end 22 of the joint dilator 20 have convex radii that complement the concave radii of the inner surfaces of arms 12. The joint dilator 20 is fully inserted into the working channel 10 when the handle 23 comes in an abutting contact with the collar 16. In this configuration, the joint dilator 20 and the working channel 10 collectively form the joint dilator assembly for insertion into the sacroiliac joint of the patient via a posterior incision. The joint dilator 20 provides structural support for the arms 12 of the working channel 10 and guides them into their position between the sacrum and ilium.

Upon proper insertion of the arms 12 of the working channel 10 into the sacroiliac joint, the joint dilator 20 is axially extracted from the lumen of the working channel 10. FIG. 4C depicts that the handle 23 is structured such that a notch 28 is formed between the collar 16 and the handle 23. The notch 28 is configured to receive the extraction tool 50, which can be used as a lever to apply an extraction force onto the handle 23.

Joint Decorticator

Figure 5A:
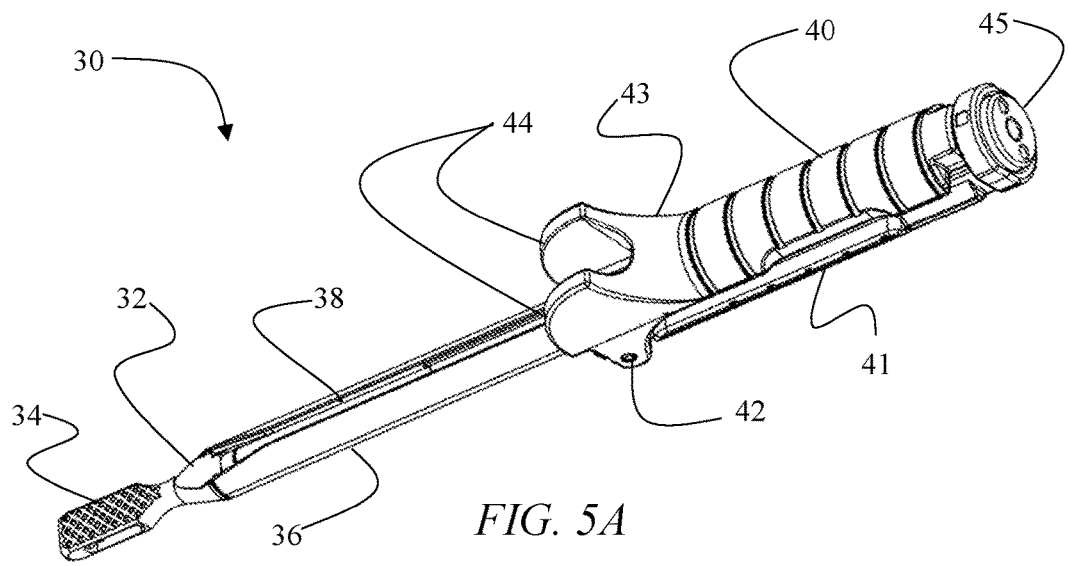
FIG. 5A is a perspective view of an embodiment of a joint decorticator.
Figure 5B:
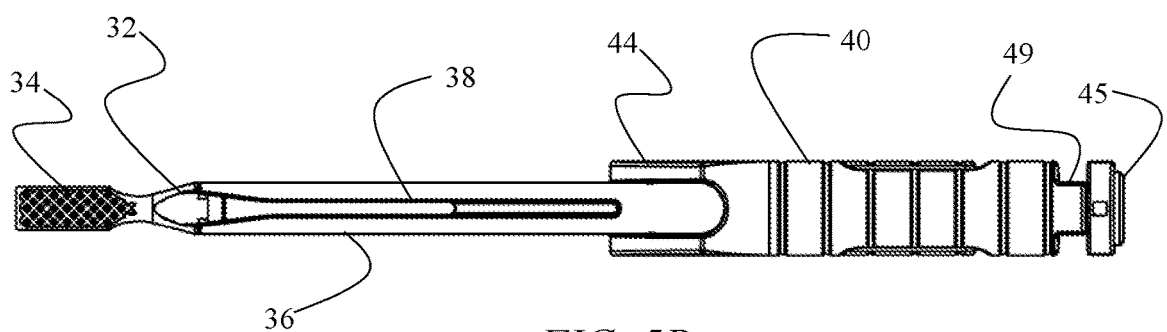
FIG. 5B is a top view of an embodiment of the joint decorticator.
Figure 5C:
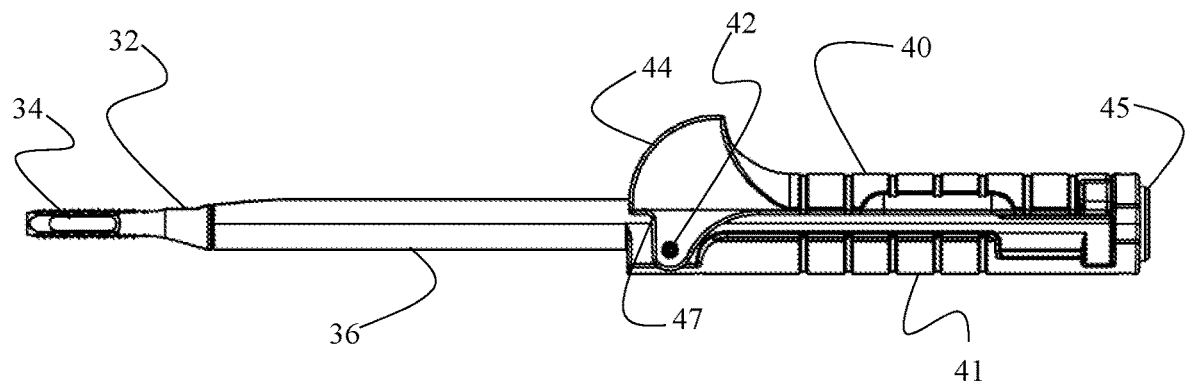
FIG. 5C is a side view of an embodiment of the joint decorticator.
Figure 5D:
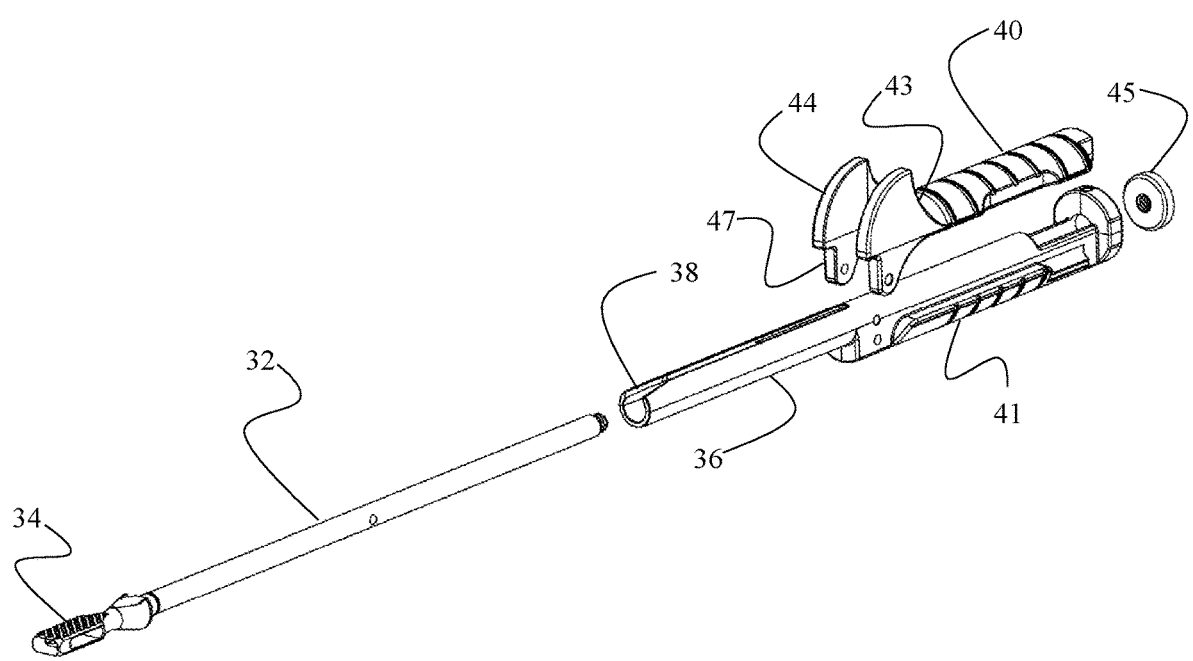
FIG. 5D is a perspective exploded view of an embodiment of the joint decorticator.

FIGS. 5A-5B depict the joint decorticator 30. The joint decorticator 30 comprises a metal rod 32. The cross-sectional shape of the rod may be circular, rectilinear, or any other shape. An abrading head 34 is disposed at the distal end of the metal rod 32. The abrading head 34 has an open tip with a sharp cutting edge configured to cut bone tissue to create an implant-receiving void within a sacroiliac joint. The cutting edge comprises one or more straight portions and one or more curved portions. The abrading head further comprises abrading surfaces configured to rasp the sacrum and ilium.

The joint decorticator 30 comprises a polymer sheath 36. The polymer sheath 36 has a lumen configured to receive the metal rod 32. The polymer sheath 36 may be affixed to the metal rod 32 using one or more fasteners, or any other fastening means known in the art. The affixed connection between the metal rod 32 and the polymer sheath 36 resists angular displacement between these two components.

The polymer sheath 36 has a longitudinal channel 38 configured for receiving the alignment protrusion 18 of the working channel 10. The longitudinal channel 38 may be flared at the distal end to help guide the alignment protrusion 18 into the longitudinal channel 38. The flared end may have a delta shape, a rounded shape, or any other shape that results in the distal opening of the longitudinal channel 38 being wider than the remainder of the longitudinal channel 38.

Decorticator Extraction Mechanism

FIGS. 5A-5D depict an extraction lever 40 pivotally connected to the polymer sheath 36 via connector pin 42, which severs as a pivot axis for the extraction lever 40. The extraction lever 40 and a handle portion 41 of the polymer sheath 36 collectively define a handle of the joint decorticator 30, which is configured to be grasped by a surgeon to articulate the joint decorticator 30 during the surgical procedure. The extraction lever 40 has a cam mechanism 44 that is disposed at its distal end. In an embodiment, the cam mechanism 44 comprises two cam-shaped members separated by a distance sufficient to accommodate the width of the polymer sheath 36 during the operation of the cam mechanism 44, as described in more detail below.

Exemplary operation of an embodiment of the decorticator 30 is shown in FIGS. 6A-6C. FIG. 6A depicts the joint decorticator 30 fully inserted inside a working channel 10. During a surgery, the working channel 10 is inserted into a patient's body such that the distal end of the working channel 10 is positioned at the target surgical site, with the sacral contour 14 and the iliac contour 15 seated against the patient's sacrum and ilium, respectively. The collar 16 at the proximal end of the working channel 10 remains outside the patient's body.

FIG. 6A further depicts that when the joint decorticator 30 if fully inserted into the working channel 10, the extraction lever 40 is in its closed position. In this fully inserted position of the decorticator 30, the abrading head 34 extends out of the lumen of the working channel 10 and is configured to make abrading contact with the sacrum and/or ilium bones of the SI joint, and preferably the respective articular surfaces of these bones. A surgeon drives the abrading head 34 into SI joint by applying an axial force onto the handle of the decorticator 30. In some instances, a surgeon may use an impact tool, such as a mallet or the joint dilator 20, to impact the proximal end of the decorticator 30, thereby driving the abrading head 34 into the SI joint. In an embodiment, an impact disk 45 is affixed to the distal end of the metal rod 32, for example via a screw-threaded engagement. The impact disk 45 protrudes beyond the distal end of the polymer sheath 36 and provides a striking surface for being impacted with the impactor. The force of the impact is transferred from the impact disk 32 to the abrading head 34 via the metal rod 32.

Due to the forceful insertion of the abrading head 34 into the SI joint, the abrading head 34 may become lodged therein. Extraction of the abrading head 34 must be performed in a controlled manner. Because counter pressure cannot be applied onto the patient's body, extraction of the abrading head 34 by applying a linear force onto the handle 41 of the joint decorticator 30 is impractical.

FIGS. 6A-6C illustrate that the extraction lever 40 can be used to achieve controlled extraction of the abrading head 34 from the SI joint. To dislodge the abrading head 34 from the SI joint, a surgeon may utilize the extraction lever 40 in the following manner: while holding the handle portion 41 of the polymer sheath 36 with one hand, the surgeon would pivot the extraction lever 40 with the other hand toward an open position, as illustrated with an arrow in FIG. 6B. When extraction lever 40 is pivoted about connector pin 42, the cam mechanism 44 exerts opposite forces onto the collar 16 of working channel 10 and the connector pin 42. As the cam mechanism 44 continues transitioning toward its open position depicted in FIG. 6C, the cam mechanism 44 pushes the connector pin 42 further away from the collar 16, thereby causing the abrading head 34 to retract into the working channel 10. After abrading head 34 is dislodged from the SI joint, the abrading tool 10 can be safely removed from the working channel 10 by pulling onto the handle 41.

FIG. 6A depicts that, when the decorticator 30 is fully inserted into the working channel 10, and the abrading head 34 is at its maximum penetration distance relative to the joint—this is the position at which the abrading head 34 is most likely to become lodged within the joint. The cam mechanism 44 is structured such that it provides the greatest mechanical advantage at the beginning of the rotation of the extraction lever 40, thereby resulting in the greater retraction force exerted onto the abrading head 34 to initiate initial dislodgement of the abrading head 34 from the joint.

In an embodiment, to reduce a likelihood of a mechanical failure the extraction lever 40 comprises fillets 43 at the interface of the cam-shaped members of the cam mechanism 44 and the handle portion 40. A person of ordinary skill in the art will recognize that by reinforcing these points of concentrated stress, the likelihood of the cam-shaped members experiencing a structural failure—i.e., breaking away from the handle portion 41 of the extraction lever 40—can be decreased. Furthermore, the redundancy achieved by including two cam-shaped members enables the extraction lever 40 to perform its intended function even if one of the cam-shaped members were to experience a structural failure.

Extraction Tool

Figure 7A:
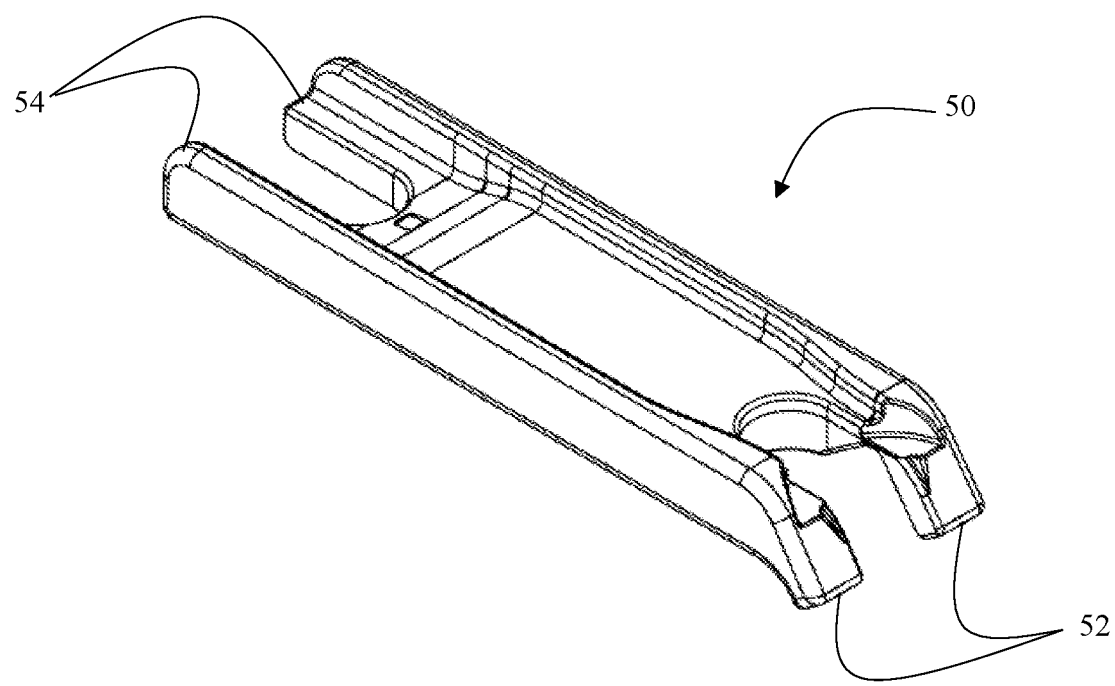
FIG. 7A is a perspective top view of an embodiment of an extraction tool.
Figure 7B:
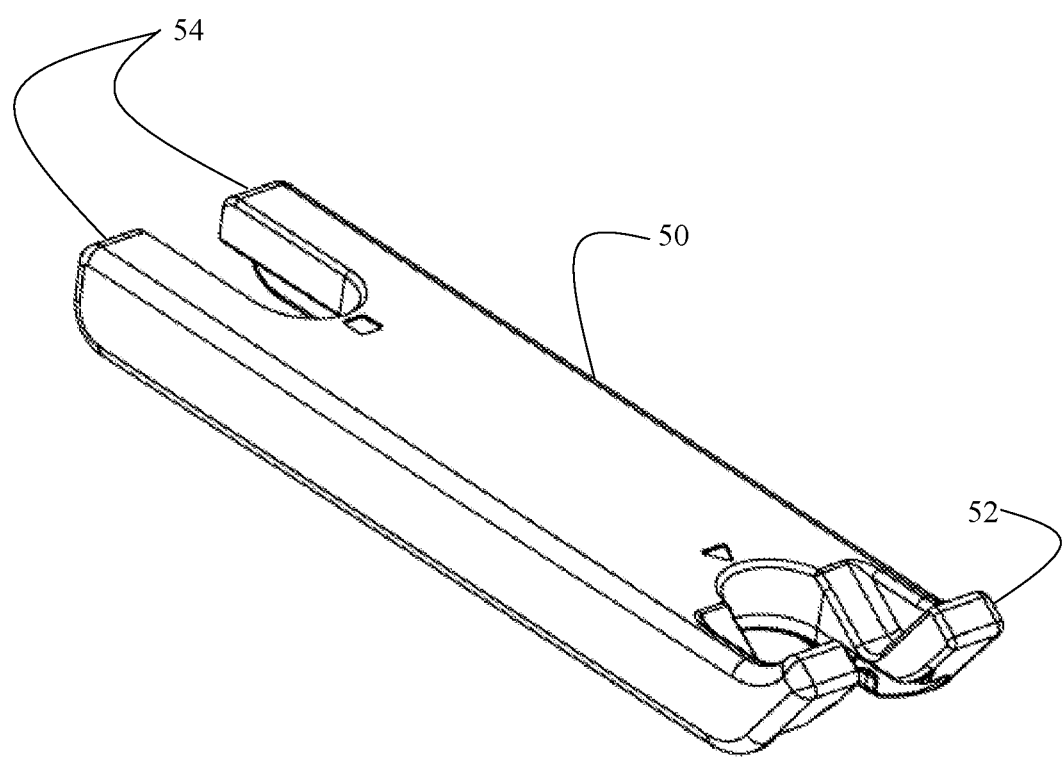
FIG. 7B is a perspective bottom view of an embodiment of an extraction tool.

FIGS. 7A and 7B depict an extraction tool 50 that can be used to dislodge the abrading head 34 of the decorticator 30 from the SI joint. The extraction tool 50 has a first pair of arms 52, a second pair of arms 54, and a body 56. The first pair of arms 52 is disposed at an angle relative to the body 56, while the second pair of arms 54 is straight relative to the body 56.

Figure 8A:
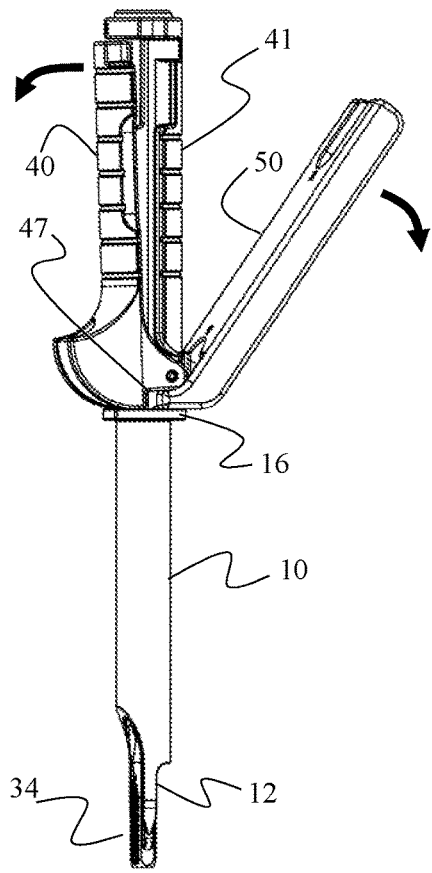
FIG. 8A is the first figure in a sequence depicting a method of using an embodiment of an extraction tool to facilitate extraction of the joint decorticator from a working channel.

FIGS. 8A-8E depict an exemplary extraction procedure using the extraction tool 50. FIG. 8A depicts that the extraction lever 40 has notches 47 shaped to receive the terminal ends of arms 52. To initiate the extraction procedure, a surgeon would insert the arms 52 into the notches 47, such that the arms 52 are positioned between the collar 16 of the working channel 10 and the cam mechanism 44. In this configuration, the body 56 of the extraction tool 50 is positioned at an angle relative to the extraction lever 40.

Figure 8B:
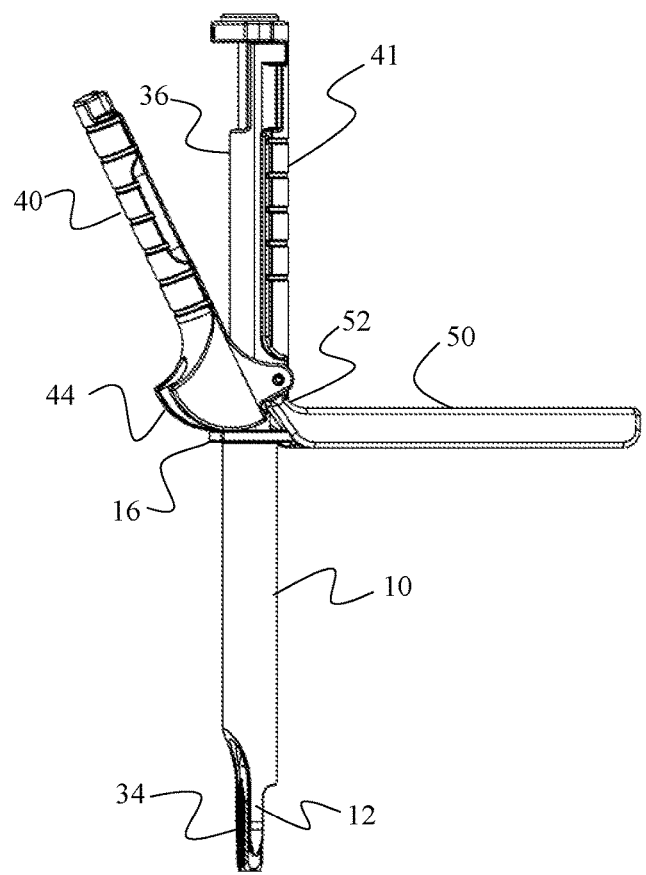
FIG. 8B is the second figure in the sequence depicting a method of using the extraction tool to facilitate extraction of the joint decorticator from the working channel.

Next, the surgeon would simultaneously apply a downward-direct force onto the body 56 of the extraction tool 50 while pivoting the extraction lever 40 toward its open position. In this manner, the extraction tool 50 functions as an additional lever increasing the magnitude of the oppositely directed forces exerted onto the collar 16 and the connector pin 42, thereby increasing the amount of retractive force applied onto the abrading head 34 of the joint decorticator 30. FIGS. 8A and 8B depict that the edge of the collar 16 serves as a fulcrum for the extraction tool 50 as the extraction tool 50 is used to extract the joint decorticator from the working channel 10.

Figures 8C, 8D, 8E:
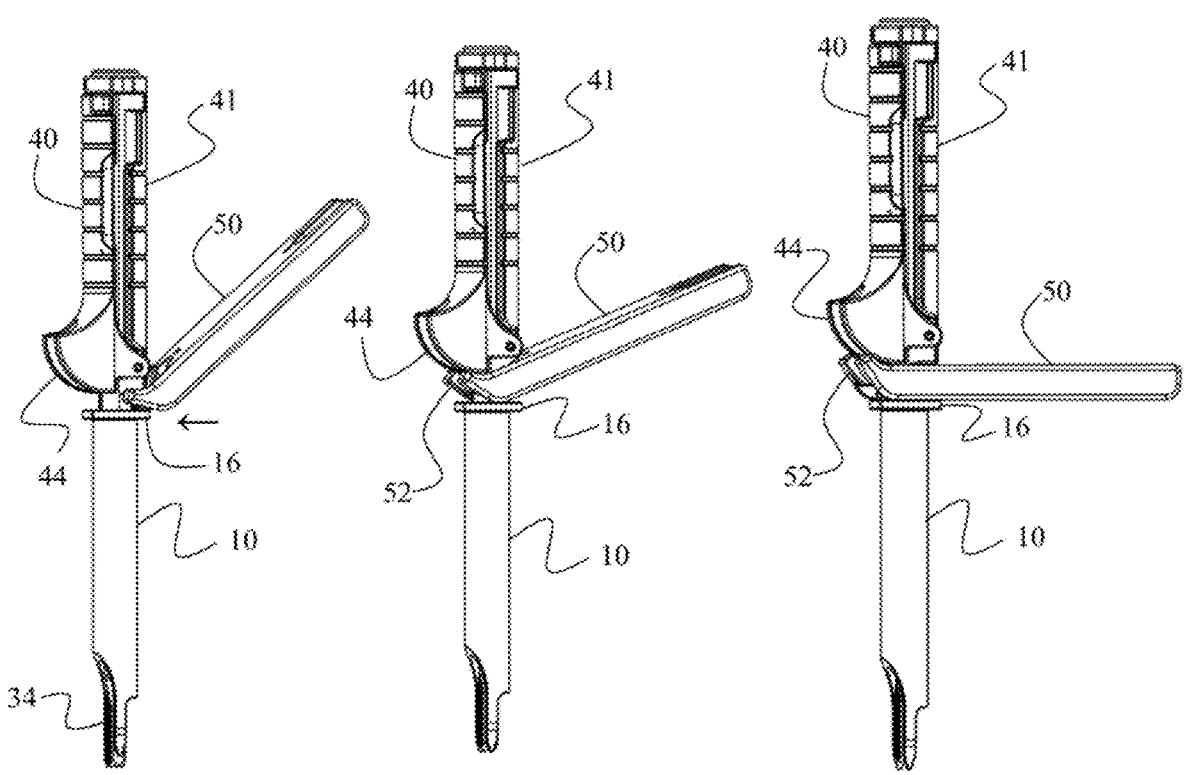
FIG. 8C is the third figure in the sequence depicting a method of using the extraction tool to facilitate extraction of the joint decorticator from the working channel.
FIG. 8D is the fourth figure the sequence depicting a method of using the extraction tool to facilitate extraction of the joint decorticator from the working channel.
FIG. 8E is the fifth figure in the sequence depicting a method of using the extraction tool to facilitate extraction of the joint decorticator from the working channel.

FIG. 8C depicts that as the distance between the distal end of the extraction lever 40 and the collar 16 increases, the extraction lever 40 can be closed, and the arms 52 of the extraction tool 50 can be inserted between the collar 16 and the extraction lever 40. In this manner, the curved edges of the cam members serve as engagement surfaces for the arms 52. FIG. 8D depicts that after the arms 52 have been positioned between the collar 16 and the extraction lever 40, the collar 16 of the working channel 10 serves at the fulcrum as the extraction tool is pivoted downward. FIG. 8E depicts that as the distance between the extraction lever 40 and the collar 16 increases, the extraction tool can be inserted further therebetween and continue to be used as a lever to continue extraction of the joint decorticator from the working channel 10.

Figure 9:
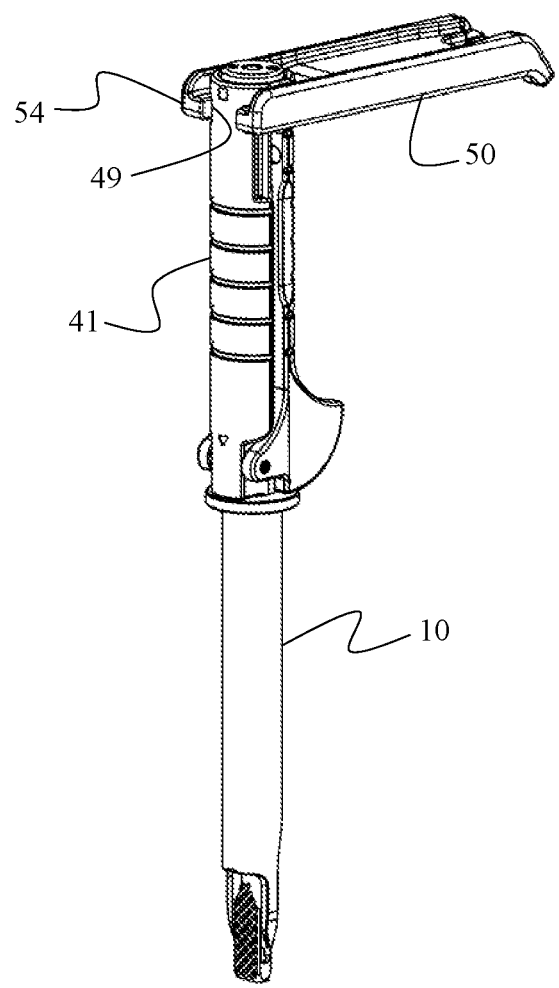
FIG. 9 depicts an alternative method of using an embodiment of the extraction tool to facilitate extraction of the joint decorticator from the working channel.

FIG. 9 depicts another method for using the extraction tool 50 to facilitate dislodgement of the abrading head 34 and extraction of the joint decorticator 30. The extraction lever 40 includes include notches 49 (most clearly depicted in FIG. 5B) near the proximal end thereof. The notches 49 are configured to receive the straight arms 54 of the extraction tool 50 such that the extraction tool 50 extends laterally from the longitudinal axis of the joint decorticator 30. In this configuration, the underside surface of the extraction tool 50 can be impacted with a mallet or another impactor (for example, the joint dilator 20) while a surgeon holds the working channel 10 stationary, thereby dislodging the abrading head 34 from the joint.

Implant Inserter

Figure 10A:
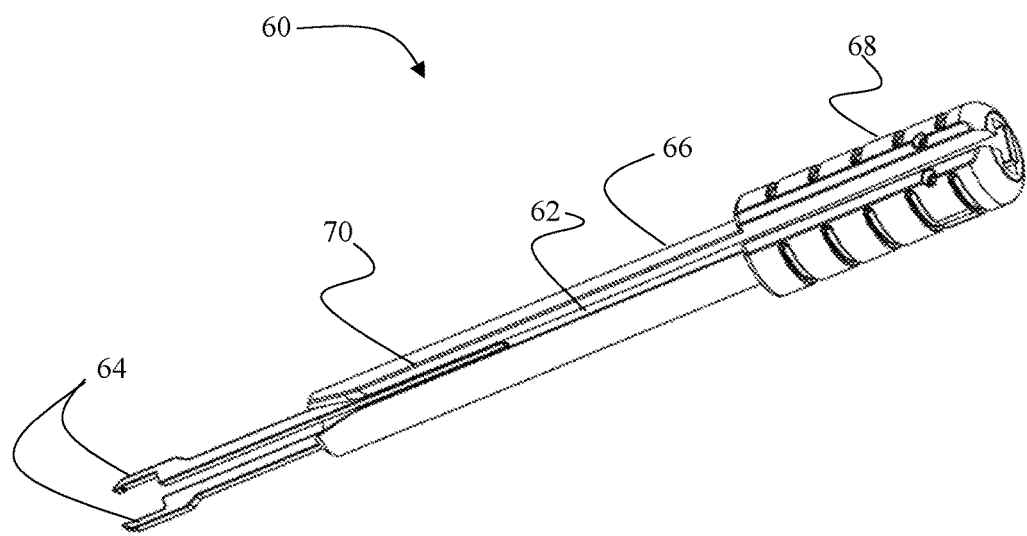
FIG. 10A is a perspective view of an embodiment of an implant inserter.
Figure 10B:
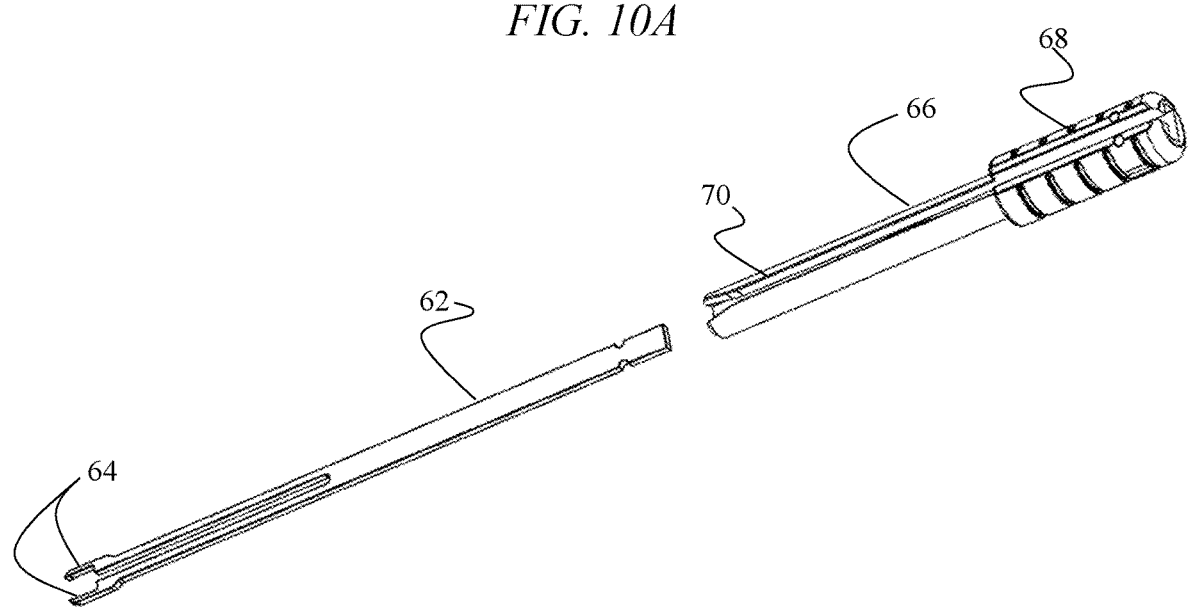
FIG. 10B is a perspective exploded view of an embodiment of the implant inserter.

FIGS. 10A and 10B depict the implant inserter 60. The implant inserter 60 comprises a metal core 62 that terminates with two implant-retaining arms 64. The implant inserter 60 further comprises a polymer sleeve 66. The polymer sleeve 66 has a lumen configured to receive the metal core 62 therein. The polymer sleeve 66 can be affixed to the metal core 62 using fasteners or any other means known in the art. The polymer sleeve has a handle 68 for articulating the implant inserter 50. The implant inserter 50 further has a channel 70 configured to receive the alignment protrusion 18 of the working channel 10 therein, thereby ensuring a predetermined radial alignment between the inserter 60 and the working channel 10. The channel 70 may be flared at the distal end to help guide the alignment protrusion 18 into the channel 38. The flared end may have a delta shape, a rounded shape, or any other shape that results in the distal opening of the channel 70 being wider than the remainder of the channel 70.

The resting distance between the arms 64 is less than the width of a fusion implant. Thus, to secure an implant within the arms 64, the arms 64 must undergo an elastic deformation to increase the separation distance therebetween to accommodate the width of the fusion implant. In this manner, when the implant is positioned between the arms 64, they apply a pressure onto the implant, thereby securely retaining the implant therebetween. The juncture at which the implant-retaining arms 64 interface with the metal core 62 is disposed within the polymer sleeve 66, whereby the polymer sleeve 66 restricts the maximum distance by which the arms 64 can be separated, thereby preventing their overextension and potential structural failure.

The dual-material construction of the surgical instruments described herein substantially reduced the cost of the instruments, making them suitable for single-use. In this manner, upon completion of a surgery the surgical instruments are discarded rather than sterilized in an autoclave. This single-use feature provides a major advantage over the state of the art by enabling medical facilities that do not have autoclaves to perform sacroiliac joint fusion procedures. In addition, by adequately stocking the single-use surgical instrument sets, a medical facility can readily ensure on-demand availability of surgery-ready instruments.

The term "metal" as used herein broadly encompasses metal and metal alloys suitable for human surgeries—for example, stainless steel or titanium. The term "polymer" as used herein broadly encompasses various polymers suitable for human surgeries, including plastics and fiber-reinforced polymers.

The foregoing embodiments are merely representative of the sacroiliac fusion instruments and are not meant for limitation of the invention. For example, persons skilled in the art would readily appreciate that there are several embodiments and configurations of the dual-material construction and the extraction mechanisms described herein. As another example, the alignment means described herein comprise channels disposed on the surgical instruments configured to receive an alignment protrusion disposed on the working channel. However, persons skilled in the art will recognize that these alignment means can be reversed, whereby the alignment protrusion can be disposed on the surgical instruments while the longitudinal channel can be disposed within the working channel. Consequently, it is understood that equivalents and substitutions for certain elements and components set forth above are part of the invention described herein, and the true scope of the invention is set forth in the claims below.

What is claimed is:

1. A decorticator apparatus for preparing a joint for receipt of a bone fusion implant, comprising:
    a polymer sheath having a lumen therein, a distal end, and a proximal end, the polymer sheath configured to be inserted into a working channel providing access to the joint;
    a metal rod disposed within the lumen of the polymer sheath in an immobilized relation thereto, the metal rod having a first end and a second end;
    an abrading head disposed on the first end of the metal rod and extending beyond the distal end of the polymer sheath, the abrading head having an abrading surface configured to abrade a cortical bone layer within the joint; and
    a longitudinal channel disposed on the polymer sheath and having an opening at the distal end thereof, the longitudinal channel configured to slidingly receive an alignment protrusion of a working channel, whereby engagement between the longitudinal channel and the alignment protrusion restricts axial rotation of the decorticator apparatus relative to the working channel thereby maintaining the abrading head of the decorticator apparatus in a predetermined alignment relative to the joint.

2. The decorticator apparatus of claim 1, further comprising an extraction lever pivotally affixed to the polymer sheath, the extraction lever having a cam mechanism configured to apply a retraction force onto the working channel as the extraction lever is pivotally transitioned from a closed position toward an open position, thereby retracting the abrading head of the decorticator apparatus into the working channel.

3. The decorticator apparatus of claim 2, wherein the cam mechanism comprises two cam members disposed on opposite sides of the polymer sheath defining a gap therebetween configured to accommodate the polymer sheath as the extraction lever is pivoted from the closed position toward the open position.

4. The decorticator apparatus of claim 2, wherein the polymer sheath comprises a first handle portion and the extraction lever comprises a second handle portion, wherein the first and the second handle portions collectively define a handle of the decorticator apparatus when the extraction lever is in the closed position.

5. The decorticator apparatus of claim 4, further comprising a fillet at an interface of the cam mechanism and the second handle portion.

6. The decorticator apparatus of claim 2, wherein in the closed position the cam mechanism is disposed on an opposite side of the metal rod relative to a pivot axis of the extraction lever.

7. The decorticator apparatus of claim 1, wherein the opening of the longitudinal channel has a delta shape configured to guide the alignment protrusion of the working channel into the longitudinal channel of the polymer sheath.

8. The decorticator apparatus of claim 1, wherein the decorticator apparatus is configured to receive an extraction tool, wherein the extraction tool is configured to simultaneously apply opposing forces onto the decorticator apparatus and the working channel, thereby causing the abrading head of the decorticator apparatus to retract into the working channel.

9. The decorticator apparatus of claim 8, wherein the decorticator apparatus has two engagement surfaces for engagement with the extraction tool, a second engagement surface being disposed at a more distal position along the decorticator apparatus relative to a first engagement surface, wherein the extraction tool is configured to sequentially operably engage the first and the second engagement surfaces, whereby each operable engagement results in an incremental extraction of the decorticator apparatus from the working channel.

10. The decorticator apparatus of claim 1, wherein the polymer sheath is configured to connect to an extraction tool, whereby the extraction tool forms a lateral surface relative to the decorticator apparatus, wherein an extraction force is applied onto the extraction tool to extract the decorticator apparatus from the working channel.

11. The decorticator apparatus of claim 10, wherein the extraction tool has an underside surface oriented toward to the distal end of the polymer sheath, and wherein the extraction force is applied by striking the underside surface of the extraction tool with an impactor.

12. The decorticator apparatus of claim 1, further comprising an impact disk disposed on the second end of the metal rod and extending beyond the proximal end of the polymer sheath, the impact disk configured for being struck with an impactor, whereby the metal rod is configured to transfer an impact force from the impact disk to the abrading head thereby driving the abrading head into the joint.

13. A method of preparing a joint for receipt of a bone fusion implant, comprising:
    inserting a working channel into the joint;
    inserting an abrading head of a decorticator apparatus into the working channel, the decorticator apparatus comprising:
        a polymer sheath having a lumen therein, a distal end, and a proximal end, the polymer sheath configured for insertion into the working channel providing access to the joint;
        a metal rod disposed within the lumen of the polymer sheath in an immobilized relation thereto, the metal rod having a first end and a second end;
        the abrading head disposed on the first end of the metal rod and extending beyond the distal end of the polymer sheath, the abrading head having an abrading surface configured to abrade a cortical bone layer within the joint;
        a longitudinal channel disposed on the polymer sheath and having an opening at the distal end thereof; and
    aligning the longitudinal channel of the decorticator apparatus with an alignment protrusion of the working channel;
    advancing the decorticator apparatus into the working channel, wherein engagement between the longitudinal channel and the alignment protrusion restricts axial rotation of the decorticator apparatus relative to the working channel, thereby maintaining the abrading head of the decorticator apparatus in a predetermined alignment relative to the joint;
    driving the abrading head of the decorticator apparatus into the joint, thereby causing the abrading head to abrade the cortical bone layer within the joint; and
    extracting the decorticator apparatus from the working channel.

14. The method of claim 13, wherein the step of extracting the decorticator apparatus from the working channel comprises pivotally transitioning an extraction lever from a closed position toward an open position, wherein the extraction lever is pivotally affixed to the polymer sheath and has a cam mechanism configured to apply a force onto the working channel as the extraction lever is transitioned from the closed position toward the open position, thereby retracting the abrading head of the decorticator apparatus into the working channel.

15. The method of claim 14, wherein as the extraction lever is transitioned from the closed position toward the open position the polymer sheath enters into a gap defined between two cam members disposed on opposite sides of the polymer sheath and collectively defining the cam mechanism.

16. The method of claim 14, wherein the step of aligning the longitudinal channel of the decorticator apparatus with the alignment protrusion of the working channel comprises the step of articulating a handle assembly of the decorticator device, wherein the handle assembly comprises a first handle portion disposed on the polymer sheath and a second handle portion disposed on the extraction lever.

17. The method of claim 15, wherein transitioning the extraction lever from the closed position toward the open position causes the extraction lever to pivot about a pivot axis disposed on the opposite side of the metal rod relative to the cam mechanism.

18. The method of claim 13, wherein the step of aligning the longitudinal channel of the decorticator apparatus with the alignment protrusion of the working channel comprises the step of positioning a delta-shaped opening of the longitudinal channel proximal to the alignment protrusion, wherein the delta-shaped opening is configured to guide the alignment protrusion of the working channel into the longitudinal channel of the polymer sheath as the decorticator apparatus is advanced into the working channel.

19. The method of claim 13, wherein the step of extracting the decorticator apparatus from the working channel comprises inserting an extraction tool between the working channel and a first engagement surface of the decorticator apparatus and pressing onto a free end of the extraction tool, wherein the extraction tool is configured to simultaneously apply opposing forces onto the decorticator apparatus and the working channel, thereby causing the abrading head of the decorticator apparatus to retract into the working channel.

20. The method of claim 19, further comprising the step of inserting the extraction tool between a second engagement surface of the decorticator apparatus and the working channel, and pressing onto the free end of the extraction tool, wherein the second engagement surface is disposed in a more distal position along the decorticator apparatus in relation to the first engagement surface.

21. The method of claim 13, wherein the step of extracting the decorticator apparatus from the working channel comprises connecting an extraction tool to the polymer sheath, wherein the extraction tool has an underside surface oriented toward the distal end of the polymer sheath, and striking the underside surface of the extraction tool with the impactor.

22. The method of claim 13, wherein the step of driving the abrading head of the decorticator apparatus into the joint comprises striking an impact disk of the decorticator apparatus, wherein the impact disk is disposed on the second end of the metal rod and extends beyond the proximal end of the polymer sheath.

* * * * *